US012408850B2

United States Patent
Hirabara et al.

(10) Patent No.: US 12,408,850 B2
(45) Date of Patent: Sep. 9, 2025

(54) PULSE OXIMETER, PULSE OXIMETRY SYSTEM, PROCESSING DEVICE, AND PULSE OXIMETRY METHOD

(71) Applicant: NIHON KOHDEN CORPORATION, Tokyo (JP)

(72) Inventors: Hideaki Hirabara, Tokorozawa (JP); Yoshiharu Harada, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 690 days.

(21) Appl. No.: 17/879,509

(22) Filed: Aug. 2, 2022

(65) Prior Publication Data

US 2023/0048928 A1    Feb. 16, 2023

(30) Foreign Application Priority Data

Aug. 10, 2021   (JP) ................................. 2021-130670

(51) Int. Cl.
*A61B 5/1455*    (2006.01)
*A61B 5/00*      (2006.01)
(Continued)

(52) U.S. Cl.
CPC ............ *A61B 5/14551* (2013.01); *A61B 5/01* (2013.01); *A61B 5/02028* (2013.01); *A61B 5/746* (2013.01)

(58) Field of Classification Search
CPC ... A61B 5/02; A61B 5/02007; A61B 5/02028; A61B 5/02416; A61B 5/1455; A61B 5/14551; A61B 5/746
See application file for complete search history.

(56) References Cited

U.S. PATENT DOCUMENTS 7,025,728 B2    4/2006 Ito et al.
8,082,017 B2*  12/2011 Messerges ......... A61B 5/02241
                                           600/324
(Continued)

FOREIGN PATENT DOCUMENTS

CN      210446999 U      5/2020
JP     2005-278758 A    10/2005
(Continued)

OTHER PUBLICATIONS

Office Action issued Dec. 17, 2024 by the Japan Patent Office in Japanese Patent Application No. 2021-130670.

*Primary Examiner* — Eric F Winakur
(74) *Attorney, Agent, or Firm* — Sughrue Mion, PLLC (57) ABSTRACT

A pulse oximeter includes a light emitting device that emits a first light and a second light, a light detecting device that outputs a first signal and a second signal respectively corresponding to an intensity of the first light and an intensity of the second light after interacting with a tissue of a subject, a processing device that calculates a pulsation rate of at least one of the first signal and the second signal, calculates a percutaneous arterial oxygen saturation of the subject, and estimates a capillary refill time of the tissue based on a time taken for at least one of the pulsation rate and the percutaneous arterial oxygen saturation, which change along with compression on the tissue, to return to a predetermined threshold range with respect to each value before the compression, and an output device that outputs information indicating the capillary refill time.

11 Claims, 4 Drawing Sheets

(51) Int. Cl.
*A61B 5/01* (2006.01)
*A61B 5/02* (2006.01)

(56) References Cited

U.S. PATENT DOCUMENTS

| | | | |
|---|---|---|---|
| 10,524,704 | B2 | 1/2020 | Ueda et al. |
| 2005/0250997 | A1 | 11/2005 | Takeda et al. |
| 2012/0130211 | A1 | 5/2012 | Kobayashi et al. |
| 2013/0018241 | A1* | 1/2013 | Bezzerides ........ A61B 5/14552 600/324 |
| 2017/0014075 | A1 | 1/2017 | Morimura et al. |
| 2020/0310098 | A1 | 10/2020 | Ince et al. |

FOREIGN PATENT DOCUMENTS

| | | |
|---|---|---|
| JP | 2012-115640 A | 6/2012 |
| JP | 2018-161512 A | 10/2018 |
| WO | 2015/137151 A1 | 9/2015 |

* cited by examiner

PULSE OXIMETER, PULSE OXIMETRY SYSTEM, PROCESSING DEVICE, AND PULSE OXIMETRY METHOD

CROSS-REFERENCE TO RELATED APPLICATIONS

The present application claims priority from Japanese Patent Application No. 2021-130670, filed on Aug. 10, 2021, the entire content of which is incorporated herein by reference.

FIELD OF THE DISCLOSURE

The present disclosure relates to a pulse oximeter configured to estimate a capillary refill time (CRT), and a pulse oximetry method. The present disclosure also relates to a pulse oximetry system and a processing device that may be used together with the pulse oximeter.

BACKGROUND

Measurement of CRT is used in the field of emergency medicine in order to determine necessity or unnecessity of fluid infusion, a priority in triage, and the like. Specifically, a medical person compresses a living tissue of a subject, such as a fingertip, and visually checks a change in the color of the skin after the compression is released. If the color returns to the original color within two seconds, it is determined that the subject is in a normal condition.

However, the method of compressing the living tissue by hands and visually checking the change in the color of the skin lacks quantification and tends to cause an error by a measurer.

Here, it has been proposed to use a pulse oximeter to estimate a CRT (see, for example, JP-A-2012-115640). Specifically, light having a wavelength absorbed by a blood is incident on a living tissue such as a fingertip, and an intensity of the light transmitted through the living tissue is measured. The blood is removed from the living tissue at a site by compression, so that the intensity of the transmitted light is increased. If the compression is released, the living tissue at the site is refilled with the blood, so that the intensity of the transmitted light is decreased. The CRT is estimated based on a time from the release of the compression until the intensity of the transmitted light returns to an original level.

SUMMARY

According to a first aspect of the presently disclosed subject matter, there is provided a pulse oximeter including a light emitting device configured to emit a first light having a first wavelength and a second light having a second wavelength different from the first wavelength, a light detecting device configured to output a first signal and a second signal respectively corresponding to an intensity of the first light and an intensity of the second light after interacting with a tissue of a subject, a processing device configured to calculate a pulsation rate of at least one of the first signal and the second signal, calculate a percutaneous arterial oxygen saturation of the subject based on the first signal and the second signal, and estimate a capillary refill time of the tissue based on a time taken for at least one of the pulsation rate and the percutaneous arterial oxygen saturation, which change along with compression on the tissue, to return to a predetermined threshold range with respect to each value before the compression, the processing device including a processor, and an output device configured to output information indicating the capillary refill time.

According to a second aspect of the presently disclosed subject matter, there is provided a pulse oximetry system including a light emitting device configured to emit a first light having a first wavelength and a second light having a second wavelength different from the first wavelength, a light detecting device configured to output a first signal and a second signal respectively corresponding to an intensity of the first light and an intensity of the second light after interacting with a tissue of a subject, and a pulse oximeter configured to calculate a pulsation rate of at least one of the first signal and the second signal, calculate a percutaneous arterial oxygen saturation of the subject based on the first signal and the second signal, and output information indicating a capillary refill time of the tissue estimated based on a time taken for at least one of the pulsation rate and the percutaneous arterial oxygen saturation, which change along with compression on the tissue, to return to a predetermined threshold range with respect to each value before the compression.

According to a third aspect of the presently disclosed subject matter, there is provided a processing device including an interface configured to receive a first signal and a second signal respectively corresponding to an intensity of a first light having a first wavelength and an intensity of a second light having a second wavelength different from the first wavelength after being emitted from a light emitting device and interacting with a tissue of a subject, and one or more processors configured to calculate a pulsation rate of at least one of the first signal and the second signal, calculate a percutaneous arterial oxygen saturation of the subject based on the first signal and the second signal, and estimate a capillary refill time of the tissue based on a time taken for at least one of the pulsation rate and the percutaneous arterial oxygen saturation, which change along with compression on the tissue, to return to a predetermined threshold range with respect to each value before the compression.

According to a fourth aspect of the presently disclosed subject matter, there is provided a pulse oximetry method including emitting a first light having a first wavelength and a second light having a second wavelength different from the first wavelength with a light emitting device, receiving, from a light detecting device, a first signal and a second signal respectively corresponding to an intensity of the first light and an intensity of the second light after interacting with a tissue of a subject, calculating a pulsation rate of at least one of the first signal and the second signal, calculating a percutaneous arterial oxygen saturation of the subject based on the first signal and the second signal, and estimating a capillary refill time of the tissue based on a time taken for at least one of the pulsation rate and the percutaneous arterial oxygen saturation, which change along with compression on the tissue, to return to a predetermined threshold range with respect to each value before the compression.

DESCRIPTION OF EMBODIMENTS

Examples of an embodiment will be described in detail below with reference to attached drawings. In the drawings referred to in the following description, a scale is appropriately changed in order to make each element recognizable.

Figure 1:
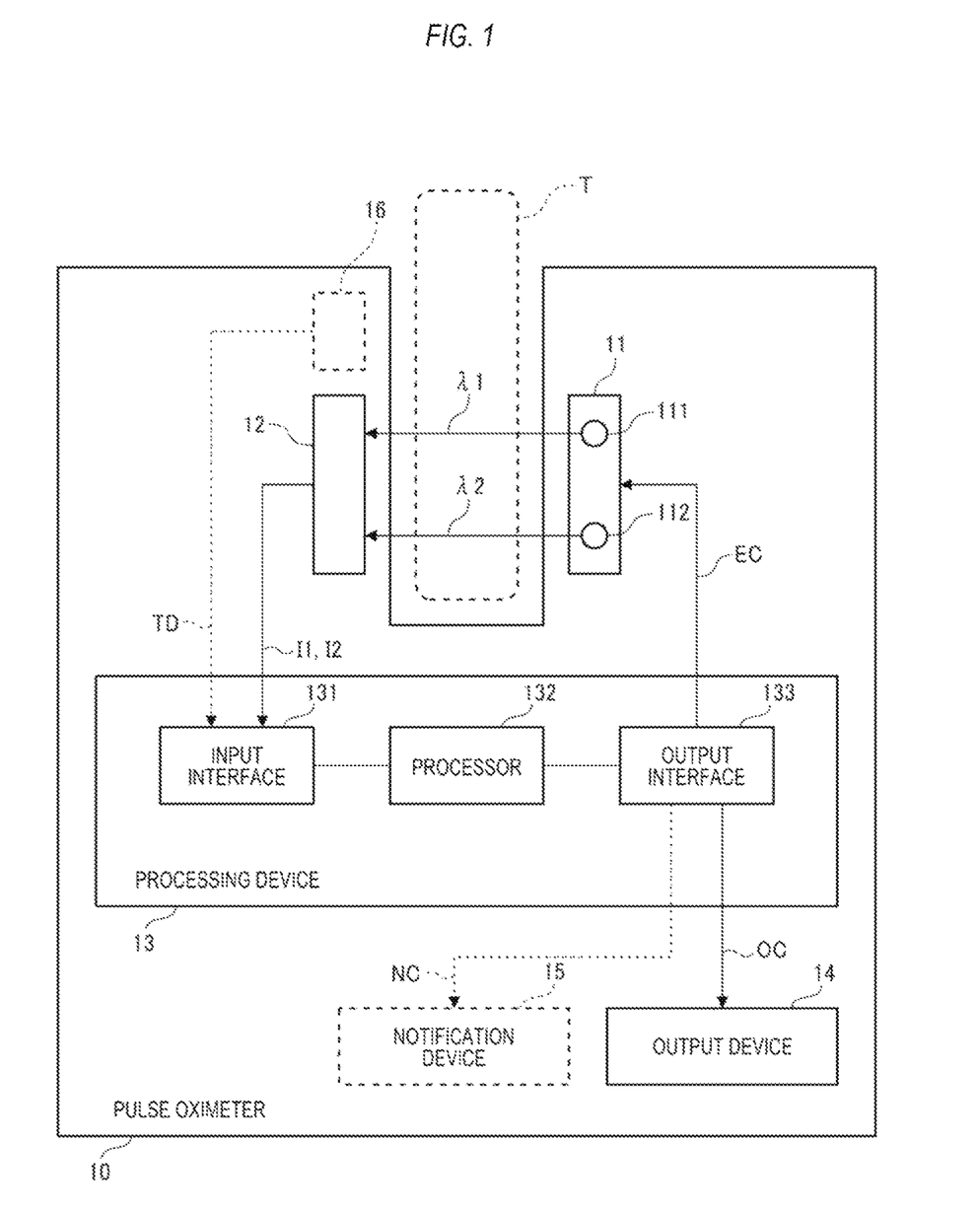
FIG. 1 illustrates a functional configuration of a pulse oximeter according to an embodiment.

FIG. 1 illustrates a functional configuration of a pulse oximeter 10 according to an embodiment. The pulse oximeter 10 is a device that calculates a percutaneous arterial oxygen saturation (SpO2) of a subject based on a concentration of a light absorber contained in an arterial blood of the subject.

The pulse oximeter 10 may include a light emitting device (light emitter) 11, a light detecting device (light detector) 12, a processing device 13, and an output device 14.

The light emitting device 11 may include a first light emitting element 111 and a second light emitting element 112. The first light emitting element 111 is configured to emit a first light having a first wavelength $\lambda 1$. The second light emitting element 112 is configured to emit a second light having a second wavelength $\lambda 2$. The light emitting device 11 may include light emitting control circuitry.

The first wavelength $\lambda 1$ and the second wavelength $\lambda 2$ are selected as two wavelengths at which a significant difference appears in an absorbance of a target blood light absorber. In the present embodiment, the first wavelength $\lambda 1$ and the second wavelength $\lambda 2$ are selected based on light absorption properties of hemoglobin required for calculation of SpO2. For example, the first wavelength $\lambda 1$ may be included in an infrared wavelength band and the second wavelength $\lambda 2$ may be included in a red wavelength band.

Each of the first light emitting element 111 and the second light emitting element 112 may be a semiconductor light emitting element. Examples of the semiconductor light emitting element include a light emitting diode, a laser diode, and an EL element.

The light detecting device 12 may include a light detecting element. The light detecting element is configured to output a first detection signal I1 and a second detection signal I2 respectively corresponding to intensities of a first light and a second light which are incident on a light detecting surface. Each of the first detection signal I1 and the second detection signal I2 may be an analog signal or a digital signal. Examples of the light detecting element include a photodiode, a phototransistor, and a photoresistor. The light detecting device 12 may include light detecting control circuitry.

The processing device 13 may include an input interface 131. The input interface 131 is configured to receive the first detection signal I1 and the second detection signal I2 output from the light detecting device 12. In a case where each of the first detection signal I1 and the second detection signal I2 is an analog signal, the input interface 131 may include an appropriate conversion circuit including an A/D converter.

The processing device 13 may include a processor 132. The processor 132 is configured to execute processing for implementing various functions described later.

The processor 132 can be implemented by a general-purpose microprocessor that operates in cooperation with a general-purpose memory. The processor 132 may include one or more processors and the memory may include one or more memories. Examples of the general-purpose microprocessor include a CPU, an MPU, and a GPU. Examples of the general-purpose memory include a ROM and a RAM. In this case, a ROM may store a computer program that executes the above processing. The general-purpose microprocessor specifies at least a part of the computer program stored in the ROM, deploys this part on a RAM, and implements the above processing in cooperation with the RAM.

The processor 132 may be implemented by a dedicated integrated circuit capable of executing the above computer program, such as a microcontroller, an ASIC, or an FPGA. In this case, the above computer program is pre-installed in a storage element included in the dedicated integrated circuit. The processor 132 may also be implemented by a combination of a general-purpose microprocessor and a dedicated integrated circuit.

The processing device 13 may include an output interface 133. The output interface 133 is configured to output a control signal for executing a predetermined operation of the light emitting device 11 and the output device 14. The control signal may be an analog signal or a digital signal. In a case where the control signal is an analog signal, the output interface 133 may include an appropriate conversion circuit including a D/A converter.

Specifically, the processor 132 outputs, from the output interface 133, a light emission control signal EC for causing the light emitting device 11 to alternately emit the first light and the second light. The first light emitting element 111 and the second light emitting element 112 alternately emit the first light and the second light at a timing specified by the light emission control signal EC.

The first light and the second light are alternately incident on a tissue T of the subject. The first light and the second light interacting with the tissue T are incident on the light detecting surface of the light detecting element. The expression of "light interacting with the tissue" is meant to include both a light transmitted through the tissue and a light reflected by the tissue.

Therefore, the light detecting device 12 alternately outputs the first detection signal I1 and the second detection signal I2. The processor 132 of the processing device 13 identifies which detection signal is received by the input interface 131 based on a timing at which light emission control of the first light emitting element 111 and the second light emitting element 112 is performed.

The processor 132 is configured to calculate a pulsation rate of the first detection signal I1 based on a change over time in an intensity of the first detection signal I1. The pulsation rate is calculated as a ratio of an alternating current component to a direct current component of the intensity of the first detection signal I1.

That is, the pulsation rate is calculated based on the first detection signal I1 corresponding to a light detecting intensity of an infrared light in the light detecting device 12. This is because the infrared light has a small difference in the light absorption properties between oxygenated hemoglobin and deoxygenated hemoglobin and is not easily affected by changes in SpO2. However, the pulsation rate may be calculated based on the second detection signal I2 depending on a situation, or the pulsation rate may be calculated for both the first detection signal I1 and the second detection signal I2, and the pulsation rate with a better condition may be selected.

In addition, the processor 132 is configured to calculate the SpO2 of the subject based on the intensity of the first detection signal I1 and an intensity of the second detection signal I2.

An intensity of the first light emitted from the first light emitting element 111 and an intensity of the second light emitted from the second light emitting element 112 have been known. Therefore, based on light detecting intensities of the first light and the second light in the light detecting device 12 corresponding to the first detection signal I1 and the second detection signal I2, a light attenuation of the first light and a light attenuation of the second light as a result of the interaction with the tissue T can be calculated. The SpO2 correlates with a ratio of the light attenuation of the first light to the light attenuation of the second light. Therefore, the SpO2 value can be calculated by inputting the ratio into a function corresponding to the correlation. The methods of calculating SpO2 value are disclosed in U.S. Pat. Nos. 7,025,728 and 10,524,704 which are incorporated by reference herein.

When the tissue T of the subject irradiated with the first light and the second light is compressed, the light attenuation of the first light and the light attenuation of the second light are changed. The compression may be performed by the user with hands or mechanically by an actuator or the like.

Figure 2:
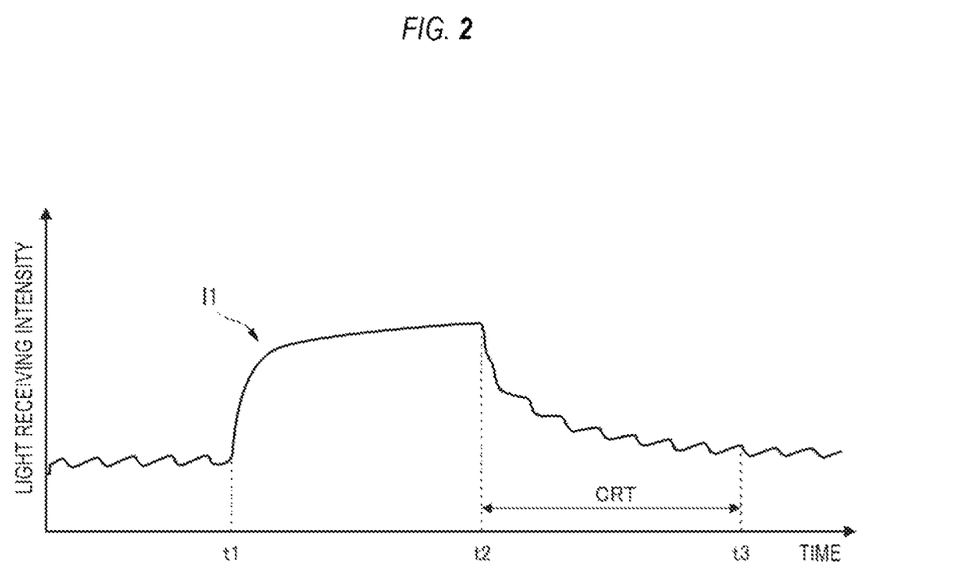
FIG. 2 illustrates a change over time in an intensity of a first detection signal in FIG. 1.

FIG. 2 illustrates a change over time in the light detecting intensity of the first light corresponding to the first detection signal I1. When the compression is started at a time t1, the blood is removed from the tissue T, and thus the light detecting intensity is increased. Along with this, the pulsation rate and the SpO2 also change. When the compression is released at a time t2, the blood returns to the tissue T, and thus the light detecting intensity is decreased. Along with this, the pulsation rate and the SpO2 also approach values before the compression.

The processor 132 is configured to specify a time from the t2 when the compression is released until both the pulsation rate value and the SpO2 value return to predetermined threshold ranges with respect to the values before the compression. FIG. 2 illustrates an example where both the pulsation rate value and the SpO2 value return to the predetermined threshold ranges with respect to the values before the compression at a time t3.

The processor 132 is configured to estimate a time from the time t2 to the time t3 as the capillary refill time (CRT) of the tissue T. As illustrated in FIG. 1, the processor 132 outputs, from the output interface 133, an output control signal OC for causing the output device 14 to output information indicating the estimated CRT.

The output device 14 is configured to receive the output control signal OC and output the information indicating the estimated CRT based on the output control signal OC. The information may be provided visually by using at least one of a text, a sign, and a color corresponding to the CRT. The visual provision of the information may be provided as an image displayed on a display or as a printed matter. In addition to or instead of the above, the information may be provided audibly by a speaker. The output device may include at least one of a display, a printer, a speaker, a lamp and output control circuitry.

Figure 3:
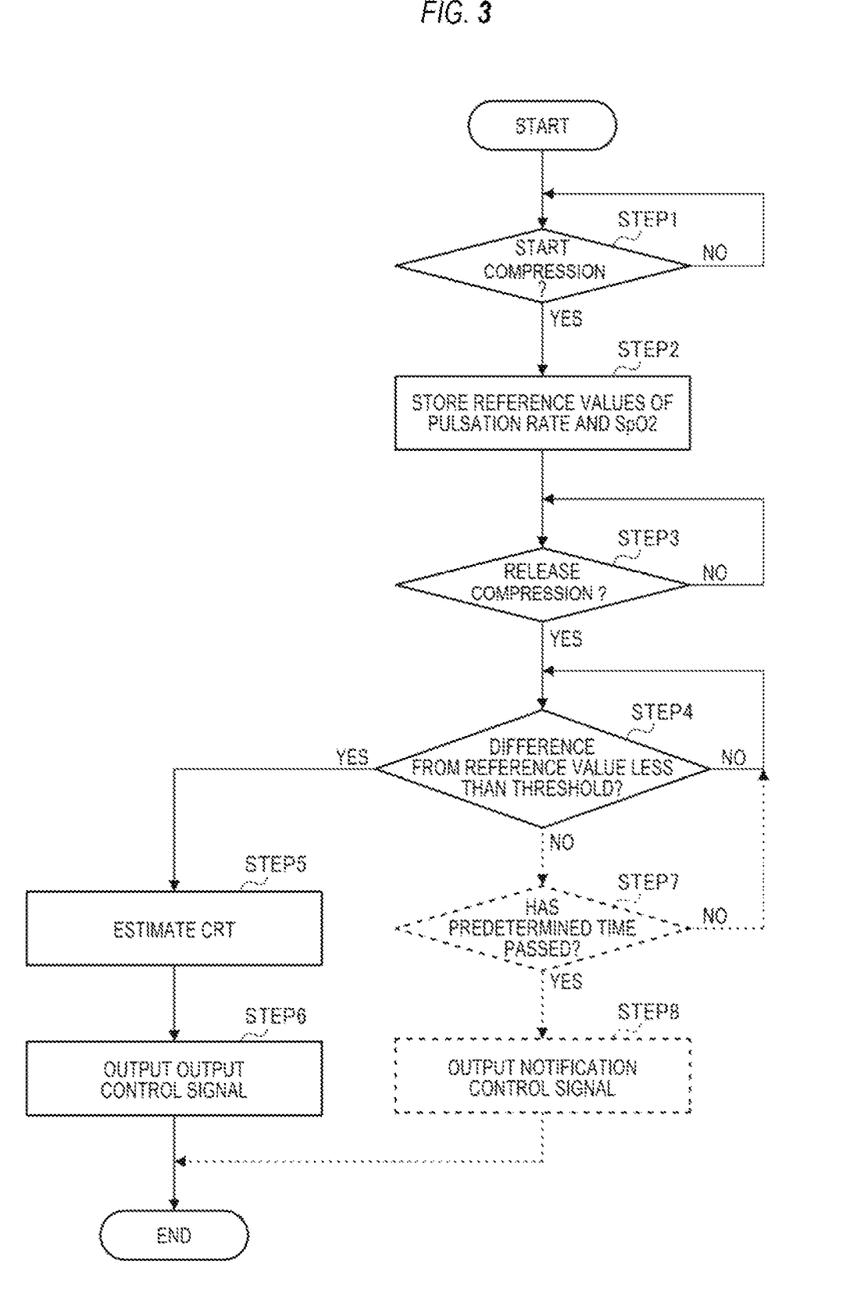
FIG. 3 illustrates a flow chart of processing executed by a processing device in FIG. 1.

FIG. 3 illustrates a flow of processing executed by the processor 132 of the processing device 13 configured as described above.

First, the processor 132 determines whether the compression on the tissue T of the subject is started (STEP 1). For example, the processor 132 may be configured to monitor a time-moving average of the intensities of the first detection signal I1 received by the input interface 131. The processor 132 determines that the compression on the tissue T is started when an amount of increase in the time-moving average per unit time exceeds a threshold. The processing is repeated (NO in STEP 1) until it is determined that the compression on the tissue T is started.

If it is determined that the compression on the tissue T is started (YES in STEP 1), the pulsation rate value of the first detection signal I1 and the SpO2 value of the subject calculated at the released time or a predetermined time before the released time are stored as reference values (STEP 2).

Subsequently, the processor 132 determines whether the compression on the tissue T is released (STEP 3). For example, the processor 132 determines that the compression on the tissue T is released when an amount of decrease in the time-moving average of the intensities of the first detection signal I1 per unit time exceeds a threshold. The processing is repeated (NO in STEP 3) until it is determined that the compression on the tissue T is released.

If it is determined that the compression on the tissue T is released (YES in STEP 3), the processor 132 determines whether a difference between each of the calculated pulsation rate value and SpO2 value and each of the reference values stored in STEP 2 is less than a threshold (STEP 4). In other words, it is determined whether the pulsation rate and the SpO2 changed with the compression return to the predetermined threshold ranges with respect to the values before the compression. The processing is repeated until the difference between the pulsation rate value and the reference value thereof is determined to be less than the threshold and the difference between the SpO2 value and the reference value thereof is determined to be less than the threshold (NO in STEP 4).

If the difference between the pulsation rate value and the reference value thereof is determined to be less than the threshold, and the difference between the SpO2 value and the reference value thereof is determined to be less than the threshold (YES in STEP 4), the processor 132 estimates, as the CRT of the subject, a time from the time when the compression on the tissue T is determined to be released in STEP 3 to the time when the difference from each of the reference values is determined to be less than the threshold in STEP 4 (STEP 5).

Subsequently, the processor 132 outputs, from the output interface 133, the output control signal OC for causing the output device 14 to output the information indicating the estimated CRT (STEP 6).

According to the configuration as described above, the CRT of the subject can be estimated by simple processing of monitoring changes over time in the SpO2 value of the subject acquired by an original function of the pulse oximeter 10, and in the pulsation rate value of the first detection signal I1 used to calculate the SpO2. Accordingly, a computation load of the processing device 13 mounted on the pulse oximeter 10 can be significantly reduced. In other words, since a required computing power can be reduced, the processing device 13 can be miniaturized and simplified while the CRT can be specified. As a result, the size and complexity of the pulse oximeter 10 can be prevented from being increased. Therefore, convenience of the pulse oximeter configured to estimate the CRT can be enhanced.

As illustrated in FIG. 1, the pulse oximeter 10 may include a notification device 15. The notification device 15 is configured to perform a notification suggesting a possibility of a hemodynamic change in the subject. The notification may be performed by at least one of a visual notification, an auditory notification, and a tactile notification. The notification device may include at least one of a display, a printer, a speaker, a lamp and notification control circuitry.

In this case, the processor 132 of the processing device 13 is configured to output, from the output interface 133, a notification control signal NC for causing the notification device 15 to perform the above notification when the time exceeds the threshold, the time is taken for the pulsation rate of the first detection signal I1 and the SpO2 of the subject, which change along with the compression on the tissue T, to return to the predetermined threshold ranges with respect to the values before the compression.

Specifically, as illustrated in FIG. 3, if it is determined that the pulsation rate and the SpO2 changing along with the compression do not return to the predetermined threshold ranges with respect to the values before the compression (NO in STEP 4), the processor 132 determines whether a predetermined length of time, from a time point when it is determined in STEP 3 that the compression on the tissue T is released, has elapsed (STEP 7).

If it is determined that the predetermined length of time has not elapsed (NO in STEP 7), the processing returns to STEP 4. If it is determined that the predetermined length of time has elapsed (YES in STEP 7), the processor 132 outputs, from the output interface 133, the notification control signal NC for causing the notification device 15 to perform the notification suggesting the possibility of the hemodynamic change in the subject (STEP 8).

If no significant hemodynamic change occurs in the subject before and after the compression on the tissue T, the pulsation rate vale and the SpO2 value will return to the values before the compression within a reasonable time after the compression is released. In other words, if the pulsation rate value and the SpO2 value do not return to the values before the compression within the reasonable time after the compression is released, it is suspected that some hemodynamic changes have occurred in the subject. According to the above configuration, the user can be notified of a possibility that such a situation has occurred according to the simple processing. Therefore, the convenience of the pulse oximeter configured to estimate the CRT can be enhanced.

As illustrated in FIG. 1, the pulse oximeter 10 may include a temperature detection device 16. The temperature detection device 16 may include a temperature sensor that detects a temperature of the tissue T of the subject. The temperature detection device 16 is configured to output a temperature detection signal TD corresponding to the temperature. The temperature detection signal TD may be an analog signal or a digital signal.

In this case, the input interface 131 of the processing device 13 is configured to receive the temperature detection signal TD as well. In a case where the temperature detection signal TD is an analog signal, the input interface 131 may include an appropriate conversion circuit including an A/D converter.

The processor 132 of the processing device 13 is configured to determine whether the temperature of the tissue T is below a threshold based on the temperature detection signal TD received by the input interface 131. The processor 132 is configured to output, from the output interface 133, a notification control signal NC for causing the notification device 15 to perform a notification suggesting a possibility that a reliability of the estimated CRT is low when the temperature of the tissue T is determined to be below the threshold.

Circulation of the blood decreases when the temperature of the tissue T of the subject is low, so that the time until the blood returns to the tissue T after the compression is released tends to be long. In this case, the estimated CRT value may be longer than the CRT value that should be originally obtained for the subject. According to the above configuration, the user can be notified of such a situation, and an opportunity to confirm the estimated CRT value can be provided. Therefore, the convenience of the pulse oximeter configured to estimate the CRT can be enhanced.

In addition, the processor 132 may be configured to determine whether the estimated CRT value exceeds the threshold. In addition to or instead of the above notification related to the reliability of the estimated CRT, the processor 132 is configured to output, from the output interface 133, a notification control signal NC for causing the notification device 15 to perform a notification suggesting a possibility that the subject has hypothermia when the temperature of the tissue T is determined to be below the threshold and the estimated value of the CRT exceeds the threshold.

If the subject has hypothermia, a tendency for the blood to return to the tissue T after the compression is released is even more prominent. Therefore, if the estimated CRT is too long, the hypothermia is suspected for the subject. According to the above configuration, the user can be notified of such a situation, and an opportunity to confirm the condition of the subject can be provided. Therefore, the convenience of the pulse oximeter configured to estimate the CRT can be enhanced.

The above embodiments are merely examples for facilitating understanding of the presently disclosed subject matter. The configurations according to the above embodiments can be appropriately changed or improved without departing from the gist of the presently disclosed subject matter.

In the above embodiments, the processing device 13 estimates the CRT of the tissue T based on the time taken for the pulsation rate and the SpO2 to return to the predetermined threshold ranges with respect to the values before the compression, the pulsation rate is calculated for at least one of the first detection signal I1 and the second detection signal I2, and the SpO2 is calculated for the subject. However, the processing device 13 may estimate the CRT of the tissue T based on the time taken for at least one of the pulsation rate and the SpO2 to return to the predetermined threshold ranges with respect to the values before the compression.

In each of the above embodiments, the light emitting device 11, the light detecting device 12, and the temperature detection device 16 are built in the pulse oximeter 10. According to such a configuration, a portability of the pulse oximeter configured to estimate the CRT can be enhanced. The effect of controlling the computation load of the processing device 13 described above can also contribute to improvement of the portability.

Figure 4:
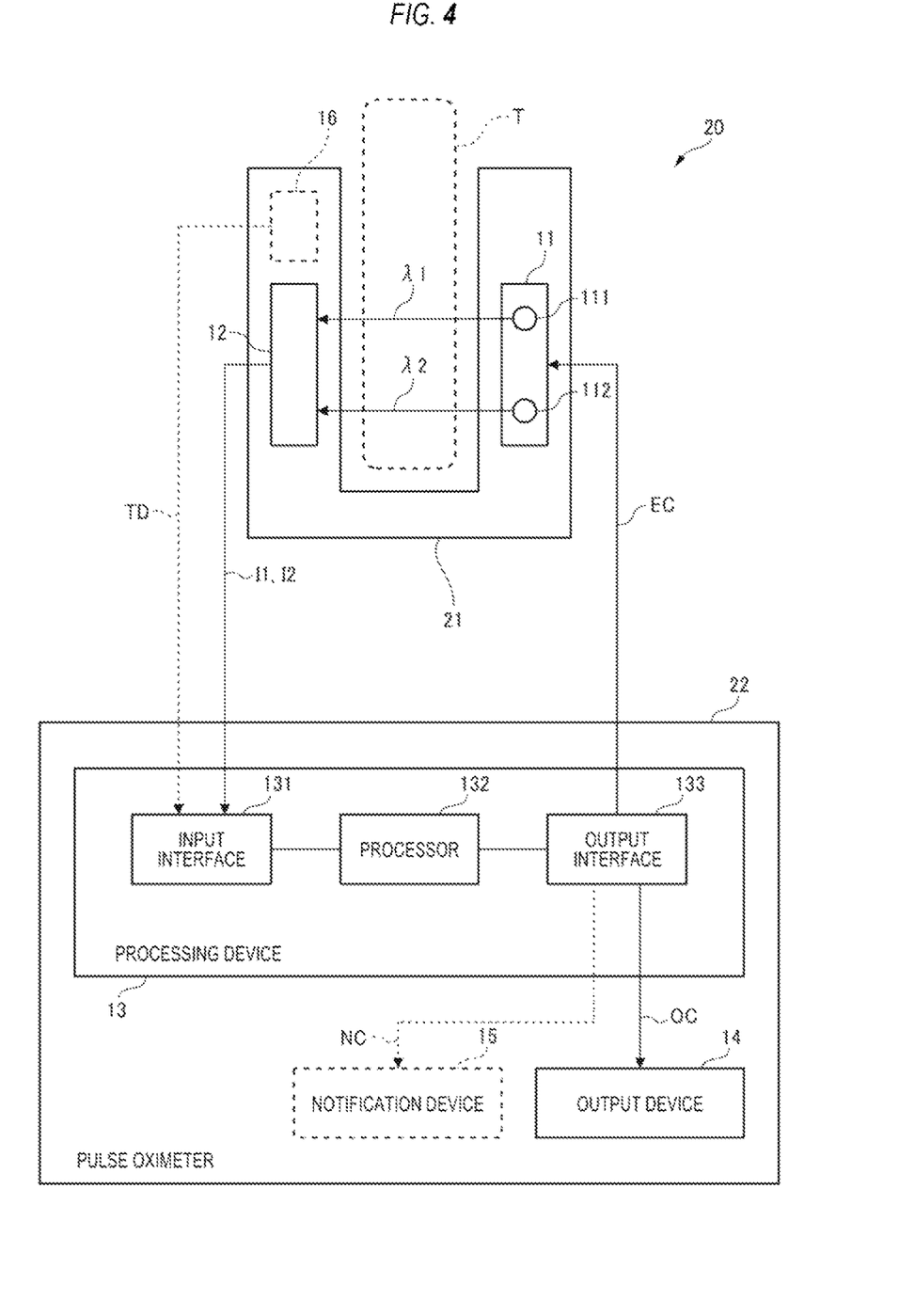
FIG. 4 illustrates a functional configuration of a pulse oximetry system according to an embodiment.

However, a pulse oximetry system 20 may be configured as illustrated in FIG. 4. The pulse oximetry system 20 may include a probe 21 and a pulse oximeter 22. The probe 21 and the pulse oximeter 22 are communicably connected.

The probe 21 is configured to be attached to the tissue T of the subject. The probe 21 may include the light emitting device 11 and the light detecting device 12 described with reference to FIG. 1. The probe 21 may include the temperature detection device 16 described with reference to FIG. 1, if necessary.

The pulse oximeter 22 may include the processing device 13 and the output device 14 described with reference to FIG. 1. The pulse oximeter 22 may include the notification device 15 described with reference to FIG. 1, if necessary.

In the embodiments described above, the processing device 13 is mounted on the pulse oximeter. However, the processing device 13 may be mounted on a device capable of data communication with the pulse oximeter. In this case, the pulse oximeter may include a communication device for data communication with the processing device 13. The first detection signal I1 and the second detection signal I2 output from the light detecting device 12 are transmitted to the processing device 13 via the communication device. The processing device 13 executes various processing described above and transmits the output control signal OC to the pulse oximeter. The pulse oximeter that receives the output control signal OC outputs, from the output device 14, information indicating the calculated SpO2 and the estimated CRT.

Regarding two entities A and B, the expression "at least one of A and B" used in the present description means that only A is specified, only B is specified, and both A and B are specified. Each entity of A and B may be singular or plural unless otherwise specified.

Regarding three entities A, B, and C, the expression "at least one of A, B, and C" used in the present description means that only A is specified, only B is specified, only C is specified, A and B are specified, B and C are specified. A and C are specified, and A. B, and C are specified. Each entity of A, B, and C may be singular or plural unless otherwise specified. The same applies to a case where four or more entities are described.

According to the configurations in the above disclosure, the capillary refill time of the subject can be estimated by simple processing of monitoring changes over time in the percutaneous arterial oxygen saturation value of the subject acquired by an original function of the pulse oximeter, and in the pulsation rate value of at least one of the first signal and the second signal used to calculate the percutaneous arterial oxygen saturation. Accordingly, a computation load of the processing device used together with the pulse oximeter can be significantly reduced. In other words, since a required computing power can be reduced, the processing device can be miniaturized and simplified while the capillary refill time can be specified. When the processing device is mounted on the pulse oximeter, a size and complexity of the pulse oximeter can be prevented from being increased. Therefore, convenience of the pulse oximeter configured to estimate the capillary refill time can be enhanced.

What is claimed is:

1. A pulse oximeter comprising:
   a light emitting device configured to emit a first light having a first wavelength and a second light having a second wavelength different from the first wavelength;
   a light detecting device configured to output a first signal and a second signal respectively corresponding to an intensity of the first light and an intensity of the second light after interacting with a tissue of a subject;
   a processing device configured to calculate a pulsation rate of at least one of the first signal and the second signal, calculate a percutaneous arterial oxygen saturation of the subject based on the first signal and the second signal, and estimate a capillary refill time of the tissue based on a time taken for at least one of the pulsation rate and the percutaneous arterial oxygen saturation, which change along with compression on the tissue, to return to a predetermined threshold range with respect to each value before the compression, the processing device including a processor; and
   an output device configured to output information indicating the capillary refill time.

2. The pulse oximeter according to claim 1, further comprising:
   a notification device configured to perform a notification suggesting a possibility of a hemodynamic change in the subject when the time exceeds a threshold.

3. The pulse oximeter according to claim 1, further comprising:
   a temperature detection device configured to detect a temperature of the tissue; and
   a notification device configured to suggest a possibility that a reliability of the capillary refill time is low when the temperature is below a threshold.

4. The pulse oximeter according to claim 1, further comprising:
   a temperature detection device configured to detect a temperature of the tissue; and
   a notification device configured to perform a notification suggesting a possibility that the subject has hypothermia when the temperature is below a threshold and the capillary refill time exceeds a threshold.

5. A pulse oximetry system comprising:
   a light emitting device configured to emit a first light having a first wavelength and a second light having a second wavelength different from the first wavelength;
   a light detecting device configured to output a first signal and a second signal respectively corresponding to an intensity of the first light and an intensity of the second light after interacting with a tissue of a subject; and
   a pulse oximeter configured to calculate a pulsation rate of at least one of the first signal and the second signal, calculate a percutaneous arterial oxygen saturation of the subject based on the first signal and the second signal, and output information indicating a capillary refill time of the tissue estimated based on a time taken for at least one of the pulsation rate and the percutaneous arterial oxygen saturation, which change along with compression on the tissue, to return to a predetermined threshold range with respect to each value before the compression.

6. A processing device comprising:
   an interface configured to receive a first signal and a second signal respectively corresponding to an intensity of a first light having a first wavelength and an intensity of a second light having a second wavelength different from the first wavelength after being emitted from a light emitting device and interacting with a tissue of a subject; and
   one or more processors configured to calculate a pulsation rate of at least one of the first signal and the second signal, calculate a percutaneous arterial oxygen saturation of the subject based on the first signal and the second signal, and estimate a capillary refill time of the tissue based on a time taken for at least one of the pulsation rate and the percutaneous arterial oxygen saturation, which change along with compression on the tissue, to return to a predetermined threshold range with respect to each value before the compression.

7. A pulse oximeter comprising:
   the processing device according to claim 6; and
   an output device configured to output information indicating the capillary refill time.

8. A pulse oximetry method, comprising:
   emitting a first light having a first wavelength and a second light having a second wavelength different from the first wavelength with a light emitting unit;
   receiving, from a light detecting unit, a first signal and a second signal respectively corresponding to an intensity of the first light and an intensity of the second light after interacting with a tissue of a subject;
   calculating a pulsation rate of at least one of the first signal and the second signal;

calculating a percutaneous arterial oxygen saturation of the subject based on the first signal and the second signal; and estimating a capillary refill time of the tissue based on a time taken for at least one of the pulsation rate and the percutaneous arterial oxygen saturation, which change along with compression on the tissue, to return to a predetermined threshold range with respect to each value before the compression.

9. The pulse oximetry method according to claim 8, further comprising:

outputting information indicating the capillary refill time.

10. The pulse oximetry method according to claim 8, further comprising:

performing a notification suggesting a possibility of a hemodynamic change in the subject when the time exceeds a threshold.

11. The pulse oximetry method according to claim 8, further comprising:

detecting a temperature of the tissue; and performing a notification suggesting a possibility that a reliability of the capillary refill time is low when the temperature is below a threshold.

* * * * *